(12) United States Patent
Tai et al.

(10) Patent No.: US 8,112,157 B2
(45) Date of Patent: Feb. 7, 2012

(54) MAGNETIC MATERIAL-CONTAINING MICROFABRICATED DEVICES FOR WIRELESS DATA AND POWER TRANSFER

(75) Inventors: Yu-Chong Tai, Pasadena, CA (US); Damien C. Rodger, Los Angeles, CA (US); Wen Li, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 1512 days.

(21) Appl. No.: 11/272,383

(22) Filed: Nov. 10, 2005

(65) Prior Publication Data

US 2006/0271129 A1 Nov. 30, 2006

Related U.S. Application Data

(60) Provisional application No. 60/685,268, filed on May 27, 2005.

(51) Int. Cl.
*A61N 1/05* (2006.01)
(52) U.S. Cl. .................. 607/53; 607/54; 607/60; 607/65
(58) Field of Classification Search .............. 607/54–55; 600/378; 329/300
See application file for complete search history.

(56) References Cited

U.S. PATENT DOCUMENTS

| | | | |
|---|---|---|---|
| 6,580,947 B1 * | 6/2003 | Thompson | 607/30 |
| 7,326,649 B2 * | 2/2008 | Rodger et al. | 438/669 |
| 7,684,868 B2 * | 3/2010 | Tai et al. | 607/54 |
| 2002/0198573 A1 | 12/2002 | Nisch et al. | |
| 2003/0100823 A1 * | 5/2003 | Kipke et al. | 600/378 |
| 2003/0141096 A1 | 7/2003 | Saccomanno | |
| 2003/0158588 A1 * | 8/2003 | Rizzo et al. | 607/54 |
| 2003/0233134 A1 | 12/2003 | Greenberg et al. | |
| 2004/0097003 A1 | 5/2004 | Kocis et al. | |
| 2004/0127001 A1 | 7/2004 | Colburn et al. | |
| 2004/0186533 A1 | 9/2004 | Greenberg et al. | |
| 2004/0229051 A1 | 11/2004 | Schaepkens et al. | |
| 2004/0263297 A1 * | 12/2004 | Glukh et al. | 335/207 |
| 2005/0121763 A1 * | 6/2005 | Ucok et al. | 257/685 |
| 2008/0169872 A1 * | 7/2008 | Ghovanloo et al. | 329/300 |

OTHER PUBLICATIONS

Williams, Kirt R. et al. (2003). *Jour of Microelectro Sys*, 12(6)761-778.

* cited by examiner

*Primary Examiner* — Carl H Layno
*Assistant Examiner* — Paula J Stice
(74) *Attorney, Agent, or Firm* — Joseph R. Baker, Jr.; Gavrilovich Dodd & Lindsey LLP

(57) ABSTRACT

This disclosure relates to the design and fabrication of microelectromechanical systems (MEMS) for applications in such varied fields as the biomedical, micro-fluidics and chemical analysis fields for wireless data and power transfer.

35 Claims, 6 Drawing Sheets

Primary (external) coil    Secondary (internal) coil

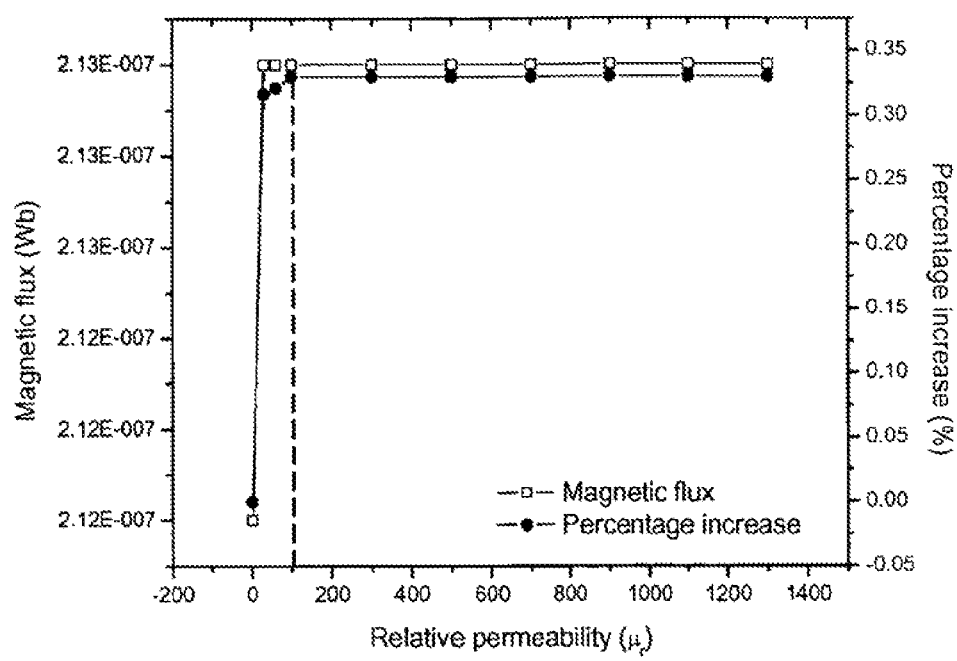
FIG. 4C
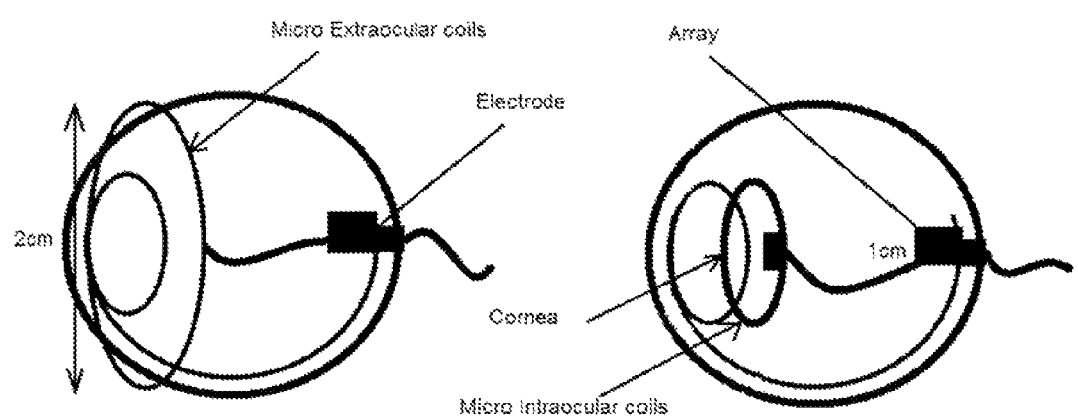
FIG. 5A
FIG. 5B

MAGNETIC MATERIAL-CONTAINING MICROFABRICATED DEVICES FOR WIRELESS DATA AND POWER TRANSFER

CROSS REFERENCE TO RELATED APPLICATIONS

This application claims priority to U.S. Provisional Application Ser. No. 60/685,268 filed May 27, 2005, the disclosure of which is incorporated herein by reference.

STATEMENTS REGARDING FEDERALLY SPONSORED RESEARCH

The invention was funded in part by Grant Nos. EEC-0310723 awarded by the National Science Foundation and by Grant No. EEC-9402726 awarded by the National Science Foundation. The government may have certain rights in the invention.

TECHNICAL FIELD

This invention relates to micro electromechanical systems (MEMS) for radio-frequency (RF) power and data transfer. The present invention further relates to methods of fabricating of such systems.

BACKGROUND

An inductive link for wireless power and data transmission generally includes a pair of radio-frequency (RF) coils, in which a primary (i.e. transmitter) coil supplies the energy in the form of a magnetic field, and a secondary (i.e. receiver) coil collects the energy from this field. For some applications the receiver coil will be positioned in an environment that requires the coil to be a very small size. Accordingly, the microfabrication of micro electromechanical systems (MEMS) that include such coils is important for applications in such varied fields as the biomedical, micro-fluidics and chemical analysis fields.

Miniaturized receiver coils useful for, e.g., transcutaneous energy transfer (TET), are generally characterized as having relatively low inductance. Accordingly, a dense magnetic field through this secondary coil is needed in order to transfer a sufficient amount of energy from the primary coil to the secondary coil. However, such a high field density might induce eddy currents in conductive materials resulting in undesired heating and damage in the materials surrounding the coil. In addition, a high input power source must be applied in the primary stage in order to generate a dense magnetic field.

The manufacture of RF coils generally includes mechanically winding metal wires into coils. However, such techniques are not suitable for the fabrication of coils capable of transferring sufficient power in the presence of less dense magnetic field. Accordingly, precise and reproducible mechanisms for microfabricating devices that concentrate the magnetic flux of a secondary coil to achieve higher power densities and efficiencies are needed.

SUMMARY

Provided herein are microdevices fabricated from non-conductive polymeric materials, magnetic materials, and conductive materials. Systems containing such devices, and methods of manufacturing such devices, are also provided. Accordingly, in one embodiment, a device that includes a conductive material configured to produce an electromotive force in the presence of a predetermined magnetic field density, is provided. The device further includes a magnetic material configured to, in the presence of a predetermined magnetic field density, increase the magnetic field density in proximity to the conductive material and induce an electromotive force in the material that is higher in the presence of the magnetic material than in the absence of the magnetic material. The device also includes a polymeric material configured to provide chemical resistance and a barrier to moisture and oxygen. In some embodiments, the magnetic material and the conductive material are completely or partially encapsulated in the polymeric material. In some embodiments, the components are assembled to provide a device that includes at least one structure that functions as a radio-frequency coil. The magnetic material is characterized as having high magnetic permeability, low coercivity, and low magnetostriction. The magnetic material may include, but is not limited to, an alloy. Alloys include nickel and iron alloys in concentrations suitable for increasing the magnetic field density. Exemplary nickel concentrations include about 80-100%, about 60-79%, about 40-59%, or about 20-39% nickel. Exemplary iron concentrations include about 80-100%, about 60-79%, about 40-59%, or about 20-39% iron.

In some embodiments, the magnetic material is selected from the group consisting of magnetic material, Fe—Ni magnetic material, Mo-magnetic material, Mu-Metal, M-1040, magnetic material and Ultraperm.

In other embodiments, the conductive material that generates a magnetic field when contacted with an electromotive force is provided. All or a portion of the conductive material is encapsulated in the polymeric material forming the device.

In some embodiments, the polymeric material includes the following properties: 1) a dielectric constant of about 2 to 4 at 60 Hz; 2) an elongation break at about 10% to 300%; and 3) a water absorption rate of about 0.01% to 0.10% per 24 hrs. The polymeric material optionally includes the following properties: 4) a tensile strength of about 30 MPa to 80 MPa; 5) a gas permeability coefficient of about 0.50 to 2000 $cm^3$-mil/100 in 24 hr at 1 atm at 23° C.; and 6) a moisture vapor transmission rate of less than 2.0 g-mil/100 in 24 hr at 90% relative humidity and 37° C. The gas may be oxygen, nitrogen, carbon dioxide, hydrogen sulfide, sulphur dioxide or chlorine. The gas permeability coefficient for oxygen is less than about 40 $cm^3$-mil/100 in 24 hr at 1 atm and at 23° C. In general, the device is suitable for, but not limited to, implantation in a biological system.

In other embodiments, the device includes a thickness from about 0.05 micron to about 50 microns, or from about 0.1 micron to about 10 microns.

In yet another embodiment, a device provided herein includes multiple layers of a non-conductive polymeric material, multiple layers of a conductive material, and/or multiple layers of a magnetic material.

The polymeric material may include at least one of a parylene, an acrylic, a siloxane, xylene, an alkene, styrene, an organosilane, an organosilazane, an organosilicone, a PDMS (poly-di-methyl-siloxane), and polyimide. In some aspects, the parylene is parylene N, parylene C, parylene D, parylene A, parylene AM, parylene F, or parylene HT. The polymeric material may be deposited by a vacuum deposition technique including, but not limited to, plasma deposition, physical vapor deposition, polymer monolithic layer deposition, and spin coating.

In another embodiment, the device includes a conductive material such as a conductive polymer, a metal, a metal oxide, a metal nitride, silicon oxide, silicon nitride, and combinations thereof. In other embodiments, conductive material comprises at least one of platinum, platinum grey, platinum black, gold, iridium, titanium, chromium, copper, aluminum, iridium oxide, chromium oxide, silver oxide, indium zinc oxide, indium tin oxide, silicon oxide, silicon nitride, silicon oxynitride, aluminum oxide, aluminum nitride, aluminum oxynitride, zinc oxide, indium oxide, tin oxide, cadmium tin oxide, cadmium oxide, and magnesium oxide, or combinations thereof.

In some embodiments, the conductive material is deposited by one of plasma deposition, physical vapor deposition, sputtering and electroplating. In other embodiments, the conductive material is deposited by one of plasma enhanced chemical vapor deposition, expanding thermal plasma, microwave plasma, inductively coupled plasma, or high density plasma chemical vapor deposition.

In one embodiment, a device provided herein includes conductive materials and non-conductive polymeric materials to form microdevices, e.g., intraocular or extraocular RF coils.

In another embodiment, a device comprising a plurality of layers of successively deposited material is provided. The deposition of each layer of material includes the deposition of at least a first polymeric material that provides chemical resistance and a barrier to moisture and oxygen. The operation further includes the deposition of at least a second conductive material that supports wireless data and power transmission. In some aspects, the conductive material is completely or partially encapsulated in the non-conductive polymeric material. The operation also includes the deposition of at least one layer of magnetic material that, in the presence of a predetermined magnetic field density, increases the magnetic field density in proximity to the conductive material and induces an electromotive force in the material that is higher in the presence of the magnetic material than in the absence of the magnetic material. Each layer is optionally selectively patterned according to the preselected structure. The device resulting from the deposition and patterning provides at least one structure that can function as a radio-frequency coil.

In another embodiment, a system including a first element comprising a device as described above, an electrode having a first end operably linked to the first element and a second end operably linked to an array, and a second element inductively linked to the first element, is provided. The second element includes a mechanism for generating a magnetic field that contacts the first element and a mechanism for generating RF telemetry that contacts the first element.

In one embodiment, the first element of the system is implanted in biological system, such as an eye. In some aspects, the device included in the first element includes a coil that receives data and/or power from the second element. The coil can be an intraocular or extraocular coil. In other embodiments, the first element further includes an integrated circuit that processes data received by the device.

In yet another embodiment, the second element is external to the biological system. In some aspects, the second element is a transmitter comprising a coil.

In one embodiment, the electrode includes a second end operably linked to an array. As used herein, an array can be any electrode contact point that accepts a signal from the electrode. Thus, the term "array" encompasses a retinal array associated with ocular tissue, such as nerve tissue associated with the retina of an eye, or other MEMS components integrated with the first and second element of the system. The first element may include an amplifier that amplifies a signal received from the second element and transmitted to the electrode for relay to an array.

In yet another embodiment, a method for manufacturing a multilayer device is provided. The method includes forming at least one layer of polymeric material on a solid substrate that may include one or more previously deposited layers of one or more materials. In some aspects, the polymeric material provides chemical resistance and provides a barrier to moisture and oxygen. The method further includes forming at least one layer of conductive material on a solid substrate that may include one or more previously deposited layers of one or more materials. In some aspects, the conductive material supports wireless data and/or power transmission. The method further includes forming at least one layer of magnetic material on a solid substrate that may include one or more previously deposited layers of one or more materials. In some aspects, in the presence of a predetermined magnetic field density, the magnetic material increases the magnetic field density in proximity to the conductive material and induces an electromotive force in the material that is higher in the presence of the magnetic material than in the absence of the magnetic material. The method also includes optionally selectively patterning each layer. The method further includes repeating the operations described above one or more times to build up a three-dimensional structure from a plurality of layers. Generally the solid substrate is removed leaving a device that includes conductive material that is completely or partially encapsulated in the polymeric material. In some aspects, the multilayer microdevice is mechanically flexible.

In some embodiments, the polymeric material includes the following properties: a dielectric constant of about 2 to 4 at 60 Hz; an elongation break at about 10% to 300%; and a water absorption rate of about 0.01% to 0.10% per 24 hrs. In other embodiments, the polymeric material comprises the following properties: a tensile strength of about 30 MPa to 80 MPa; and a gas permeability coefficient of about 0.50 to 2000 $cm^3$-mil/100 in 24 hr at 1 atm at 23° C.

In one embodiment, the conductive material generates an electromotive force when contacted with a modulated magnetic field. In other embodiments, the conductive material generates a magnetic field when contacted with an electromotive force.

In other embodiments, the conductive material is formed by one of plasma deposition, physical vapor deposition, sputtering, or electroplating. In some aspects, the plasma deposition is plasma enhanced chemical vapor deposition, expanding thermal plasma, microwave plasma, inductively coupled plasma, or high density plasma chemical vapor deposition.

In other embodiments, the conductive material is patterned by a liquid reagent or a gaseous reagent. In some aspects, the gaseous reagent is plasma.

In some embodiments, the solid substrate is comprised of silicon, glass, steel, quartz, soda lime or Teflon, or derivatives thereof. In some aspects, the silicon is low expansion titanium silicate.

In one embodiment, the polymeric material layer is formed by one of plasma deposition, physical vapor deposition, polymer monolithic layer deposition, or spin coating.

In other embodiments, the magnetic material layer is formed by one of plasma deposition, physical vapor deposition, polymer monolithic layer deposition, spin coating or screen printing.

In other embodiments, the polymeric material is patterned by a plasma liquid reagent, a gaseous reagent, laser ablation, or blade cutting.

In other embodiments, a method of manufacturing a device of the invention further includes heat treating the multilayer device to conform to a region of implantation in a biological environment.

In one embodiment, methods of manufacturing devices of the invention include metal-etch fabrication processes. In other embodiments, the methods include lift-off fabrication processes.

In other embodiments, methods for manufacturing a device are provided. The methods include providing a solid substrate, optionally depositing a resist (i.e., sacrificial) layer on the substrate, and depositing a layer of polymeric material on the optional first resist layer or the substrate. The methods further include depositing a layer of a magnetic material on the non-conductive polymeric material and subsequently depositing a layer of conductive material on the layer of polymeric material. The methods also include patterning the multiple layers of materials by processes known to those skilled in the art of integrated circuit manufacturing. For example, multiple layers of conductive, magnetic and polymeric materials can be deposited and patterned such that the final product can function as a wireless transceiver of power and/or data. It is understood that the deposition and patterning processes can be accomplished by, for example, lift-off or metal-etch techniques.

In some embodiments the solid substrate includes silicon, or derivatives thereof such as low expansion titanium silicate. In other embodiments, the solid substrate can be glass, steel, quartz, soda lime or Teflon.

In another embodiment, a resist layer can be patterned by a liquid reagent or a gaseous reagent. The gaseous reagent can be, for example, plasma.

In yet another embodiment, methods of the invention further comprise heat treating the microdevice to conform to a region of implantation in a biological environment.

In another embodiment, provided herein are devices manufactured by a method of the invention.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 4C depicts relative permeability of a magnetic material versus magnetic flux for two exemplary coil geometries.

FIG. 5A depicts a system of the invention including an extra-ocular device.

FIG. 5B depicts a system of the invention including an intra-ocular device.

Like reference symbols in the various drawings indicate like elements.

DETAILED DESCRIPTION

As will be described in more detail below, a device that includes a non-conductive polymeric material, a magnetic magnetic material, and a conductive material that generates an electromotive force when contacted with a modulated magnetic field, or alternatively generates a magnetic field when contacted with an electromotive force, is provided. Systems containing the device and methods of manufacturing the device are also provided.

Figure 1:
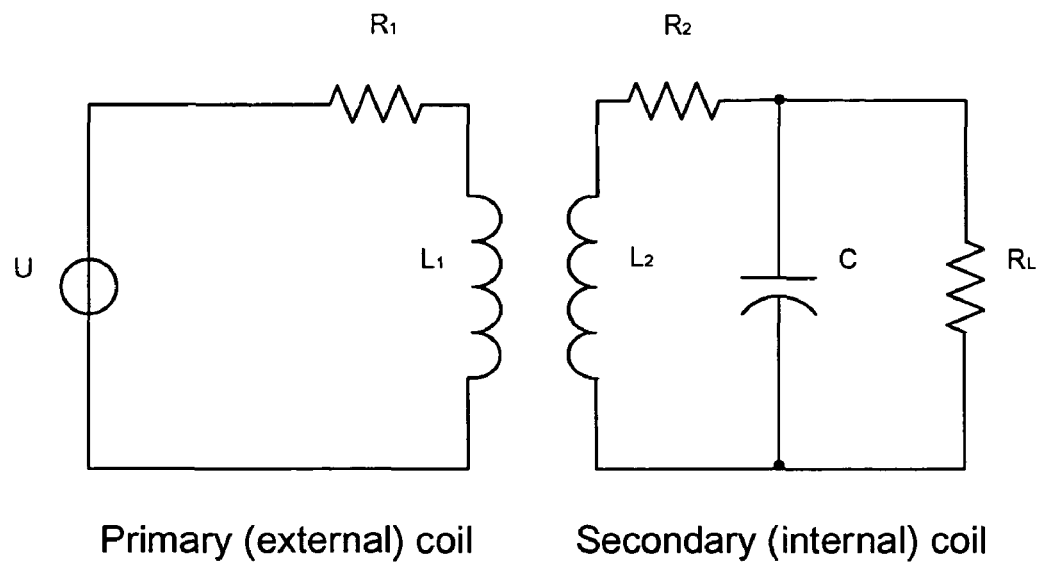
FIG. 1A depicts an electromagnetically coupled power system.
FIG. 1B depicts an electromagnetically coupled power system as utilized in one embodiment of the invention.
Figure 1:
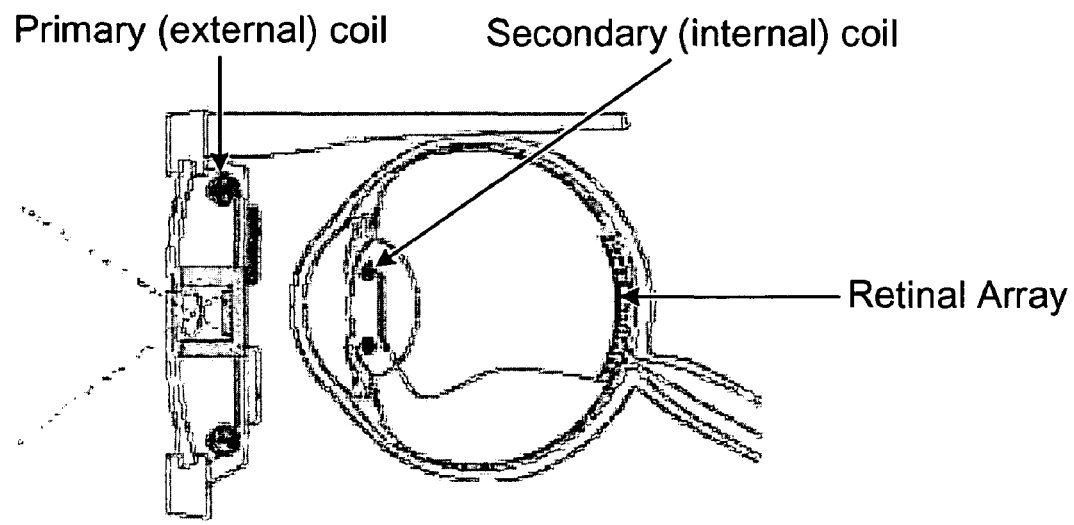

Referring to FIG. 1A and FIG. 1B, the devices and systems provided herein are designed for use with wireless power and data transmission. An electromagnetically coupled power system is implemented in practice through the use of an inductive link, which is effectively a weakly coupled coreless transformer.

In one embodiment, a device of the invention is a transceiver that includes a secondary coil suitable for receiving power and data from an external source. Optionally, the device may transmit data to the an external source. To optimize the power transfer system, the secondary coil may be designed to have high inductance (L2) and low resistance (R2). Exemplary equations for implementation of a device of the invention are given as:

$$R = \rho \frac{L}{A_c},$$

$$V = -\frac{d\Phi}{dt} = -NA\frac{dB}{dt} = -NA\mu_0 H_{amp}\omega,$$

$$L_2 = 2\pi d N^2 \times 10^{-9} \left[ \left( \ln\frac{4d}{t} \right)\left( 1 + \frac{t^2}{24d^2} \cdots \right) - \frac{1}{2} + \frac{43t^2}{288d^2} \cdots \right] (Henries),$$

R is the coil resistance, ρ is the resistivity, L is the total coil length, $A_c$ is the cross section of the coil, N is the number of turns, A is the projective coil area, $\mu_o$ is the vacuum permeability, $H_{amp}$ is the magnetic field amplitude, ω is the angular frequency of the AC signal (i.e., 2π×1 MHz for the current system), $L_2$ is the secondary coil inductance, d (in cm) is the diameter of the coil, and t (in cm) is the coil width.

Based, in part, upon information derived from the above-identified equations, the incorporation of a magnetic material in proximity to a conductive material in a device of the invention provides for improved power generation in the presence of a predetermined magnetic field density. The magnetic material effectively concentrates the magnetic flux to achieve higher power densities and efficiencies in devices provided herein. Referring to FIG. 2D and FIG. 2E, a device of the invention includes a conductive material configured to produce an electromotive force in the presence of a predetermined magnetic field density. The device further includes an magnetic material configured to, in the presence of a predetermined magnetic field density, increase the magnetic field density in proximity to the conductive material and induce an electromotive force in the material that is higher in the presence of the magnetic material than in the absence of the magnetic material. The device also includes a polymeric material configured to provide chemical resistance and a barrier to moisture and oxygen. In some embodiments, the magnetic material and the conductive material are completely or partially encapsulated in the polymeric material. In general, the components are assembled to provide a device that includes at least one structure that functions as a radio-frequency coil.

As used herein, the term "configured" is defined as the amount and geometry of a particular material organized so as to function in accordance with the role of the material in a device of the invention. For example, a material is "configured" for operating in a device of the invention by depositing specified amounts of the material in particular patterns. It is understood that the function of a first material in a device may be modified by altering the amount and/or geometry of the material. In addition, it is understood that the function of the first material in a device may be modified by altering the amount and/or geometry of a second material in the device. For example, the configuration (e.g., amount and/or geometry) of a conductive material will impact the ability of the material to produce an electromotive force in the presence of a predetermined magnetic field density. Similarly, the configuration (e.g., amount and/or geometry) of a magnetic material in proximity to the conductive material may impact (i.e., modify) the ability of the conductive material to produce an electromotive force in the presence of a predetermined magnetic field density. It is also understood that the amount of a material used in a device, and the geometry of the material, can be varied according to the size and shape of the device.

As used herein, the term "proximity" means that one material in a device is near enough to another material in the device such that each material can impact or modify the function of the other material. For example, a magnetic material is in "proximity" to a conductive material when the magnetic material is near enough to the conductive material to modify the ability of the conductive material to produce an electromotive force in the presence of a predetermined magnetic field density. It is understood that a first material need not be in direct or physical contact with a second material in order for the first material to impact the function of the second material. This is exemplified in the structures provided in FIG. 2D and FIG. 2E.

Accordingly, the amount and geometries of the magnetic material as included in the device can be determined using, for example, finite-element simulations in FEMLAB. As described throughout the specification, a device of the invention can be microfabricated using multi-layer non-conductive polymer/conductive material thin film technology, which enables further integration with MEMS devices, ASICs and discrete components to facilitate a system solution for both biomedical and non-biomedical applications. Exemplary structure 1, as shown in FIG. 2D provides one possible configuration for the component materials included in a device of the invention. In exemplary structure 1, multiple rings of conductive material 40 are encompassed by layers of magnetic material 35. Exemplary structure 2, as shown in FIG. 2E provides another possible configuration for the component materials. In this example, the magnetic material 35 is distributed between rings of conductive material in order to achieve vertical distribution of a magnetic field. These structures were determined by simulations using high magnetic flux and induced current parameters. It is understood that additional structures can be devised using similar calculations and simulations.

"Magnetic material," as used herein, includes any permmagnetic material of alloy and non-alloy. An exemplary magnetic material may include, for example, varying amounts of nickel and iron. Alternatively, the material may include only a single type of metal, such as nickel. A magnetic material included in a device of the invention can be characterized as having a high magnetic permeability, low coercivity, near zero magnetostriction, and displays magnetoresistive characteristics. One exemplary alloy is permalloy. Generically, permalloy refers to a magnetic material with about 20% iron and about 80% nickel content. This magnetic material is used in transformer laminations and anisotropic magnetoresistive (AMR) sensors. Its electrical resistivity generally varies within the range of 5% depending on the strength of the magnetic field. Other types of magnetic material are available and designated by a numerical prefix denoting the percentage of nickel in the magnetic material. For example, "45" permalloy, containing 45% nickel, and 55% iron. Permalloy's permeability can be enhanced by heat treatment. Additional magnetic material include Fe—Ni Magnetic material, Mo-Perm-magnetic material, Mu-Metal, M-1040, Supermagnetic material, Ultraperm.

In order to form a closed circuit with two perimeter contacts, two layers of conductive material can be fabricated using metals or other conductive materials, such as conductive polymers. The layers of conductive material can be in configured as a "coil" in the device because such a configuration creates a dense magnetic field (high magnetic flux) in contrast to a straight conductor. However, it is understood that devices provided herein are not limited solely to a "coil" configuration for the conductive material. For example, a device may include a conductive material that possesses the attributes necessary to operate as a "coil," as described above, without actually maintaining a "coil" configuration. Such configurations, while generally circular, also include oval, square, rectangular, or any other configuration suitable for supporting RF data and/or power transfer via inductance. The devices provided herein are suitable for manufacture using techniques and equipment ordinarily used in the manufacture of integrated circuits (IC) and other MEMS devices. Similar to an IC, the structure of a device of the invention is limited only by the material used to manufacture the device and the techniques used to deposit and pattern such material. Accordingly, methods provided herein may be used to manufacture devices that include conductive material in a "non-coil" arrangement yet retain the functionality of a conventional hand-wound coil.

Figure 4A:
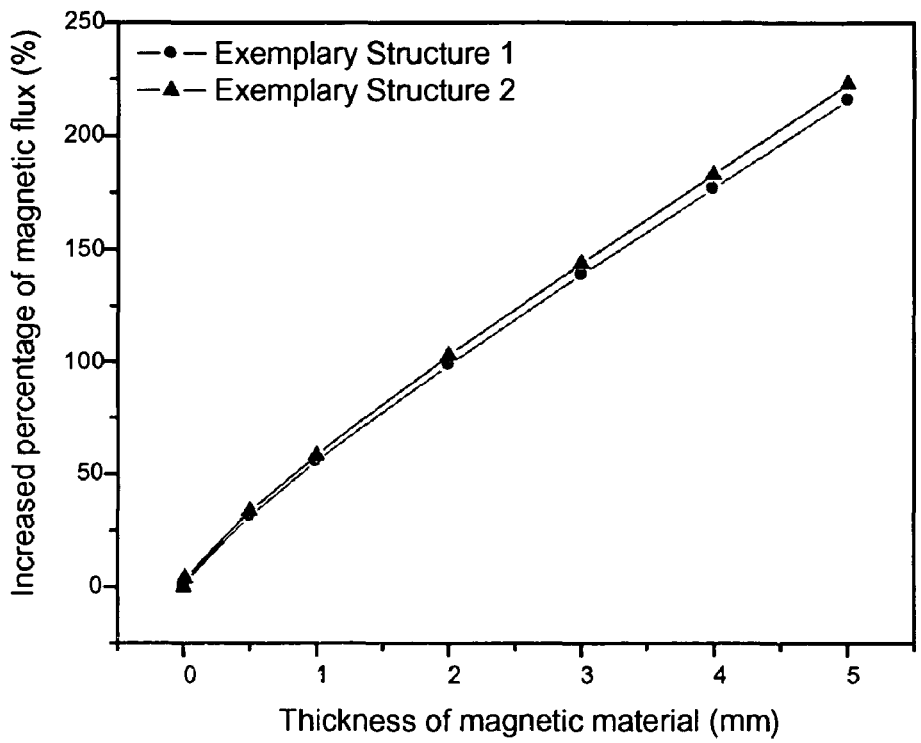
FIG. 4A depicts increased percentage of magnetic flux versus thickness of magnetic material for two exemplary coil geometries.
Figure 4B:
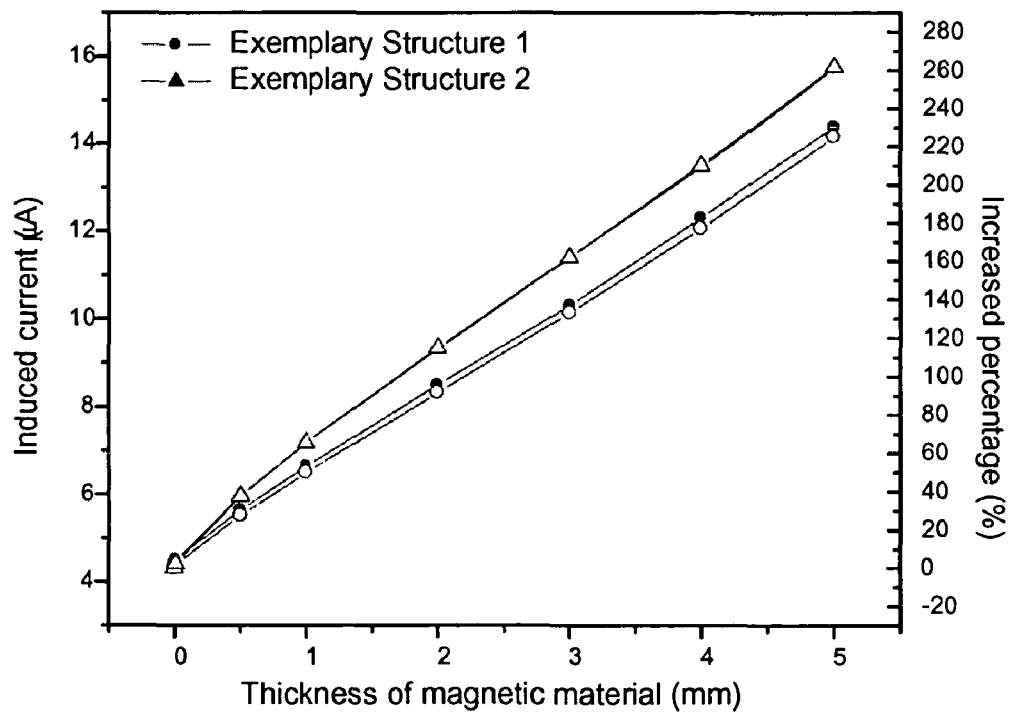
FIG. 4B depicts induced current versus thickness of magnetic material for two exemplary coil geometries.

Referring to FIG. 4A, the magnetic flux through conductive material (e.g., a coil) and induced currents as functions of thickness of magnetic material layers can be simulated for the two exemplary configurations as shown in FIG. 2D (exemplary structure 1) and FIG. 2E (exemplary structure 2). In addition, FIG. 4B shows induced current versus thickness of magnetic material for both exemplary configurations. Finally, FIG. 4C shows increased percentage of magnetic flux versus thickness of magnetic material in a device for both exemplary configurations.

While the conductive material used in the exemplary configurations is about 12 mm in outer diameter, it is understood that the precise dimension can be varied for different applications. According to the simulation results, a thicker magnetic material layer(s) can achieve a denser magnetic flux, and thus a higher induced current in the coil. As described below, such layer(s) can be deposited using electroplating technology, spin-coating, sputtering, or other techniques known to the skilled artisan. Accordingly, the magnetic material can be deposited in a structure comprising multi-layer magnetic material thin films.

Referring to FIG. 4C, the magnetic flux through the conductive material becomes stable when the relative permeability of the magnetic material is higher than a value of about 100. Therefore, lower permeability magnetic materials without iron, such as nickel, can be used to fabricate the magnetic layers of a device by considering the compatibility and stability of the materials in various applications, such as biomedical applications. Examples of such applications are shown in FIG. 5A and FIG. 5B.

The conductive material can be interconnected via contact defined using oxygen plasma etching. Polymers (e.g. parylene) can be used as insulating and packaging materials, and different coil profiles can be defined using oxygen plasma etching or excimer laser ablation, or other available techniques. Finally, the whole thin film can be released from substrate using a resist material as a sacrificial layer. For the further integration with other MEMS devices, ASICs and discrete electrical components, the connection pads can be replaced by flexible cables fabricated using polymer/metal/polymer thin film techniques The non-conductive polymeric material of the device serves to isolate the conductive layer from exposure to biological environments containing corrosive substances, such as salt, and the like. Such external elements can cause the destruction and degradation of the conductive layer over time through tarnishing, breakdown, or delamination, resulting in the loss of its conductivity.

In general, the polymeric material possesses chemical and physical properties consistent with biocompatibility and flexibility, and is suitable for micromachining. Such properties may include a dielectric constant of about 1 to 5, 2 to 4, or about 3 at 60 Hz. An elongation-at-break of about 1% to 500%, 5% to 400%, 10% to 300%, or about 200%. A water absorption rate of about 0.001% to 2%, 0.01 to 0.1%, or about 0.01% to 0.10% per 24 hrs. A tensile strength of about 1 MPa to 100 MPa, 30 MPa to 90 MPa, or about 50 MPa to 80 MPa. A gas permeability coefficient of about 0.10 to 2000, 0.20 to 100, or about 0.3 to 10 $cm^3$-mil/100 in 24 hr at 1 atm at 23° C. The gas may be oxygen, nitrogen, carbon dioxide, hydrogen sulfide, sulphur dioxide or chlorine. For example, the polymeric material may possess a gas permeability coefficient for oxygen of about 1 to 10, 2 to 9, 4 to 8, or about 7 $cm^3$-mil/100 in 24 hr at 1 atm and at 23° C. In general, the device is suitable for, but not limited to, implantation in a biological system.

Additional properties of the polymeric material may include a moisture vapor transmission rate of less than about 2.0, 1.0, or about 0.5 g-mil/100 in 24 hr at 90% relative humidity and 37° C.

Exemplary polymeric material includes flexible polymers such as parylene polymer, acrylic, siloxane, xylene, alkene, styrene, organosilane, organosilazane, organosilicone, PDMS (poly-di-methyl-siloxane), and polyimide. Polyimide is widely used in electrical ribbon interconnects, because of its heat tolerance, mechanical strength, and chemical stability. PDMS is chemically similar to various forms of silicone rubber that exhibit high chemical stability. Parylene is a material that is commonly deposited conformally using plasma deposition and thus can coat any contour with a thin film that has properties similar to that of a plastic bag. Parylenes are chemically inert, biocompatible, flexible and have a relatively low gas permeability. Parylene polymers include parylene N, parylene C, parylene D, parylene A, parylene AM, parylene F, parylene HT, or combinations or mixtures thereof. For example, a parylene polymer layer can be composed of an interpolymer of monomers of parylene variants of varying mixture ratios. The thickness of the parylene polymer layer may range from a few thousand angstroms to about 75 microns. More specifically, a parylene polymer layer can be about 0.0001 micron, 0.001 micron, 0.01 micron, 0.1 micron, or 1 micron to about 75 microns. It is noted that the actual thickness of and the mixture ratios of the variants in the parylene polymer layer can be adjusted according to the application, requirements, the conductive component used, the desired effect, the duration of effect, and the types of expected contaminant exposures and the like, and may be readily determined by one skilled in the art.

In accordance with the present invention, non-conductive polymeric materials can be applied in layers through a coating process using conventionally known vapor phase deposition or vacuum evaporation deposition techniques. It is understood that the present invention can utilize any suitable commercially available method for applying a polymer to a surface as known by one skilled in the art. The deposition process can be repeated at least once using the same or a different polymeric material (e.g., parylene N, parylene C, parylene D, parylene A, parylene AM, parylene F, parylene HT, and/or mixtures thereof) to produce a multilaminate polymeric coating. Exemplary deposition techniques include plasma deposition, physical vapor deposition, polymer monolithic layer deposition, and spin coating. Also included are plasma enhanced chemical vapor deposition, expanding thermal plasma, microwave plasma, inductively coupled plasma, and high density plasma chemical vapor deposition.

A "non-conductive polymeric material," as used herein, is defined as a material composed of large molecules that have been formed from the chemical bonding of smaller units (monomers). In addition, the material possesses a low K dielectric. Examples of low K dielectric materials include, fluorine-doped silicate glass (FSG), xerogels and other porous oxide materials, silsesquioxanes, organosilicates, parylene, fluorinated materials, among other low K dielectrics. The dielectric strength of an insulating material is the maximum electric field strength that it can withstand intrinsically without breaking down, i.e., without experiencing failure of its insulating properties.

A device of the invention manufactured with a non-conductive polymeric material, a conductive material and a magnetic material, as described herein, can be optionally processed using suitable annealing or heat-treatment techniques to improve the chemical resistance and durability of the polymeric layer. The term "annealing" or "heat-treating" as used herein refers to any processes for treating a substance or material with heat followed by cooling to modify or alter the structural properties of the treated substance or material. The device may be fashioned such that it conforms to the shape of the tissue in which implantation will occur. For example, the device may be fabricated to include a concave shape so that it conforms to the foveal pit of an eye.

Referring to the device 50 of FIG. 2D and the device 60 of FIG. 2E, the invention further includes a conductive material 40 that receives power/and or data from an external source by inductively coupled radio-frequency (RF) telemetry. Thus, the conductive material 40 generates an electromotive force when contacted with a modulated magnetic field. Alternatively, the conductive material 40 generates a magnetic field when contacted with an electromotive force. The conductive material can include at least one of a conductive polymer, a metal, a metal oxide, a metal nitride, silicon oxide, silicon nitride, and combinations thereof. Exemplary metals include chromium oxide, silver oxide, indium zinc oxide, indium tin oxide, silicon oxide, silicon nitride, silicon oxynitride, aluminum oxide, aluminum nitride, aluminum oxynitride, zinc oxide, indium oxide, tin oxide, cadmium tin oxide, cadmium oxide, platinum, platinum grey, platinum black, gold, iridium, titanium, chromium, copper, aluminum, iridium oxide, magnesium oxide and combinations thereof.

As previously noted, an electromagnetically coupled power system is implemented in practice through the use of an inductive link, which is effectively a weakly coupled coreless transformer. A transformer is an electrical device that transfers energy from one electrical circuit to another by magnetic coupling without moving parts. Referring to FIG. 1A and FIG. 1B, a single phase (1ϕ) transformer generally includes two electrical conductors called the primary coil (external) and the secondary coil (internal). The primary is fed with a varying (alternating or pulsed direct current) electric current which creates a varying magnetic field around the conductor. According to the principle of mutual inductance, the secondary, which is placed in this varying magnetic field, will develop a potential difference called an electromotive force (EMF). If the ends of the secondary are connected together to form an electrical circuit, this EMF will cause a current to flow in the secondary. Thus, some of the electrical power fed into the primary is delivered to the secondary.

A device of the invention may include multiple layers of a polymeric material, multiple layers of a conductive material, and multiple layers of a magnetic material. In view of the methods provided herein, the skilled artisan can readily determine the number and thickness of layers necessary to form a device suitable for receiving data a power from another source. In general, the device can have a thickness from about 0.05 micron to about 50 microns, or from about 0.1 micron to about 100 microns.

In another embodiment, a device comprising a plurality of layers of successively deposited material is provided. The deposition of each layer of material includes the deposition of at least a first polymeric material that provides chemical resistance and a barrier to moisture and oxygen. The operation further includes the deposition of at least a second conductive material that supports wireless data and power transmission. In some aspects, the conductive material is completely or partially encapsulated in the polymeric material. The operation also includes the deposition of at least one layer of magnetic material that, in the presence of a predetermined magnetic field density, increases the magnetic field density in proximity to the conductive material and induces an electromotive force in the material that is higher in the presence of the magnetic material than in the absence of the magnetic material. Each layer is optionally selectively patterning each layer according to the preselected structure. The device resulting from the deposition and patterning provides at least one structure that can function as a radio-frequency coil.

Devices of the invention can be included in any system that requires the wireless transfer of power and/or data. Accordingly, a system including a first element comprising a device as described above, an electrode operably linked to the first element, and a second element inductively linked to the first element, is provided. The second element includes a mechanism for generating a magnetic field that contacts the first element and a mechanism for generating RF telemetry that contacts the first element, or a mechanism for generating an electromotive force when contacted by a magnetic field from the first element.

Referring to FIG. 1A, the primary (external) coil provides an exemplary second element of a system provided herein. With regard to vision restoration, the second element can take the form of a prosthesis that includes a primary coil located either in an eyeglass lens frame or in a soft contact lens (see e.g., FIG. 1B). The primary coil is used to inductively couple, for example, a radio frequency encoded image signal to a device containing a secondary coil that, in some embodiments, is implanted behind the iris of the eye (see e.g., FIG. 1B and FIG. 5B). The power supply for the implant is obtained by rectification and filtering of the received radio-frequency signal. Digital data transmission to the implant is achievable by, for example, modulating the RF carrier signal. Reverse transmission can be implemented by varying the load seen by the secondary of the transformer.

Referring again to FIG. 5A and FIG. 5B, the device containing the secondary coil (e.g., a micro extraocular coil or micro intraocular coil) can be operably linked to an electrode, such as a macular electrode. FIG. 5A and FIG. 5B show two components of a system of the invention, the first element (e.g., a device including a coil) and an electrode (e.g., a macular electrode) operably linked to an array, such as a retinal array associated with the retina of the eye. The first element optionally includes an integrated circuit that processes data received by the device before transmission to the electrode. In one aspect, the integrated circuit can be programmed to translate the details of a captured visual image into a pattern of stimulation. This pattern information may then be transferred to the retina via the electrode.

Referring to FIG. 1B, the first element may include a retinal array interposed between the electrode and the retina. The retinal array is operably associated with the electrode and functionally associated with retinal tissue. Retinal arrays can be broadly divided into two categories: epi-retinal and sub-retinal. Epi-retinal devices are placed on or near the inner surface of the retina, e.g., the side which is first exposed to incoming light rays and along which the nerve fibers of the ganglion cells pass on their way to the optic nerve. Sub-retinal devices are placed under the retina, between the retina and the underlying retinal pigment epithelium or other deeper tissues. The retinal array may include an integrated circuit for translating the details of a captured visual image into a pattern of stimulation of the retina. A retinal array may obtain sufficient power from a device of the invention to both operate the electronics and stimulate the retina.

Accordingly, a retinal array can include intrinsic microcircuitry that could provide: 1) stimulus control in a manner that mimics natural retinal function; 2) stimulation that creates center-surround neural responses; 3) spatial filtering; 4) stimuli that generate retinal responses like those influenced by natural light-dark adaptation; 5) algorithmic commands as received from external sources; 6) stimuli that track movement of objects with the visual environment; 7) reverse telemetry of hardware and biological function, including but not limited to electrode resistance, temperature, pH, neural activity, presence neurotransmitters or other biochemicals; and 8) and other functions that would either contribute to creation of vision or monitor the safety or effectiveness of the implanted device.

The retinal array generally contains stimulating elements (e.g., microelectrodes) in, for example, a grid-like pattern. Optionally, the retinal array can contain light-sensitive elements, such as photodiodes, interlaced together with the stimulating elements. Such retinal arrays are discussed in more detail in U.S. Patent Application Pub. No. 2003/0158588, which is incorporated herein by reference, in its entirety. Alternatively, the light sensitive elements of a system of the invention can be positioned outside the eye. Accordingly, the light sensitive elements may be associated with a device worn externally by a subject. For example, the light sensitive elements may be mounted near the exterior RF primary coil (i.e., the secondary element), although such an arrangement is not required. The exterior RF coil, for example, may be mounted on the side of a pair of eyeglasses (or on a similarly placed supporting structure, or, in an alternate embodiment, under the skin) near and parallel to an implanted RF secondary coil. The primary coil can be driven by an external transmitter circuit carried by the subject.

In some embodiments a device of the invention, as incorporated in to a system of the invention, may receive only power from the primary coil and deliver only power to the other components of the primary element (e.g., integrated circuit(s), electrodes and/or retinal arrays). In this mode, a second "RF data" secondary coil can be included in a system of the invention. An RF data secondary coil can be manufactured according to the methods provided herein.

Alternatively, a single device of the invention, as incorporated in to a system of the invention, may receive power and image information (e.g., data). Generally a system of the invention will include electronic circuitry for producing a set of electrical patterns in response to inputted image information. Subsequently, an electrical signal is conveyed to, for example, microelectrodes associated with a retinal array. The electronic circuitry may be included in the secondary element or the primary element of the system. The circuitry will generally include one or more transformation algorithms and parameters of the algorithms by which the optical pattern of the inputted image information is converted to a pattern of electrical stimulation that can be convey to the retina.

As previously noted, an exemplary system of the invention includes an external assembly (i.e., a second element) directly or indirectly attached to the body of the patient and an internal assembly (i.e., a first element) which is implanted in the patient. The internal assembly typically includes an internal coil, an electrode, and a retinal array positioned in or on the recipient's retina.

Collectively, the external coil and the internal coil form an inductively-coupled coil system for transcutaneous transfer of data and/or power. The transfer of energy via this system is controlled to effect the transmission of the electrical coded signals, referred to herein as stimulation signals, and power signals from an external image processing unit to the implanted unit. Once a stimulation signal has been transmitted to the implanted coil, it can be provided to an implanted integrated circuit which processes the signal and outputs one or more signals to the electrode which may apply the electrical stimulation directly to the retina of the recipient or directly to a retinal array associated with the retina of the recipient.

It is understood that the ocular implant system described above, and shown, in part, in FIGS. 5A and 5B, is exemplary only. A device provided herein may be included in any system that supports the use of a transceiver that includes a non-conductive polymeric material and a conductive material that generates an electromotive force when contacted with a modulated magnetic field, or generates a magnetic field when contacted with an electromotive force. The devices and systems provided herein are particularly well-suited for use in a biological environment, but they are not limited to such environments. For example, the array operably linked to the electrode can in principle be anything, such as living tissue, MEMS components, application-specific integrated circuits (ASICs), multi-electrode arrays or, as described above, a retinal array. Accordingly, a system of the invention provides a mechanism for the wireless transmission of power and data from a source (i.e., a second element) to a receiver (i.e., a first element), through an electrode and ultimately to an array capable of accepting electrical stimulation and/or digital data from the electrode.

In other embodiments, methods for fabricating a device of the invention are provided. The device is designed to be part of an inductively-coupled radio-frequency system that includes at least one secondary coil encased in an polymeric material. In one aspect, the device is implantable in a biological system. In one example, the biological system is an ocular system and the device resides either extraocularly or intraocularly. The device is considered to be an "implant" as long as it is intimately associated with a biological environment, such as ocular tissue. The device may be fashioned such that it conforms to the shape of the tissue in which implantation will occur. For example, the device may be fabricated to include a concave shape so that it conforms to the foveal pit of an eye.

The devices provided herein include a conductive material, such as a conductive polymer or metal, and a non-conductive polymeric material, such as parylene. With regard to a device of the invention, the conductive material is completely or partially encapsulated in the non-conductive material such that it is protected from an environment, such as a biological environment, while maintaining the ability to receive data and power from an external source. Methods for manufacturing such a device include deposition, pattern replication and etching processes known to those skilled in the art of fabricating MEMS devices and integrated circuits (IC). Exemplary methods of manufacturing devices and systems of the invention are discussed below.

Accordingly, in yet another embodiment, a method for manufacturing a multilayer device is provided. The method includes forming at least one layer of polymeric material on a solid substrate that may include one or more previously deposited layers of one or more materials. In some aspects, the polymeric material provides chemical resistance and provides a barrier to moisture and oxygen. The method further includes forming at least one layer of conductive material on a solid substrate that may include one or more previously deposited layers of one or more materials. In some aspects, the conductive material supports wireless data and power transmission. The method further includes selectively patterning the conductive material, and optionally selectively patterning the polymeric material. In some aspects, the operation of depositing and patterning can be repeated one or more times to build up a three-dimensional structure from a plurality layers. The method further includes removing the solid substrate. The resulting multilayer device is mechanically flexible. In addition, the conductive material is completely or partially encapsulated in the polymeric material.

In general, the conductive material generates an electromotive force when contacted with a modulated magnetic field. Alternatively, it may generate a magnetic field when contacted with an electromotive force.

As previously noted, the conductive material includes at least one of a conductive polymer, a silicon derivative, or combinations thereof. In some aspects, the conductive material includes at least one of a platinum, platinum grey, platinum black, gold, iridium, titanium, chromium, copper, aluminum, iridium oxide, chromium oxide, silver oxide, indium zinc oxide, indium tin oxide, silicon oxide, silicon nitride, silicon oxynitride, aluminum oxide, aluminum nitride, aluminum oxynitride, zinc oxide, indium oxide, tin oxide, cadmium tin oxide, cadmium oxide, magnesium oxide, and combinations thereof.

The conductive material can be formed by one of plasma deposition, physical vapor deposition, sputtering, or electroplating. Plasma deposition processes include, but are not limited to, plasma enhanced chemical vapor deposition, expanding thermal plasma, microwave plasma, inductively coupled plasma, or high density plasma chemical vapor deposition. The conductive material can be patterned by a liquid reagent or a gaseous reagent, such as plasma.

The polymeric material includes at least one of a parylene, an acrylic, a siloxane, xylene, an alkene, styrene, an organosilane, an organosilazane, an organosilicone, a PDMS (poly-di-methyl-siloxane) or a polyimide. In some aspects, the parylene is parylene N, parylene C, parylene D, parylene A, parylene AM, parylene F, parylene HT, or combinations thereof. The polymeric material layer can be formed by one of plasma deposition, physical vapor deposition, polymer monolithic layer deposition, or spin coating. The polymeric material can be patterned by a plasma liquid reagent, a gaseous reagent, laser ablation, or blade cutting.

The materials and techniques provided herein are uniquely suited to manufacturing a device that can be molded in to particular shapes. Heat treating a device manufactured by a method provided herein is one mechanism for molding such devices. Accordingly, manufacturing a device of the invention further includes heat treating the multilayer device to conform to a region of implantation in a biological environment.

Figure 2A:
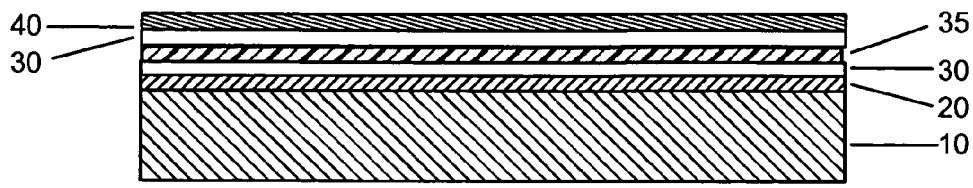
FIGS. 2A, 2B and 2C show material deposition for microfabrication of a device of the invention.
Figure 2B:
Figure 2B:
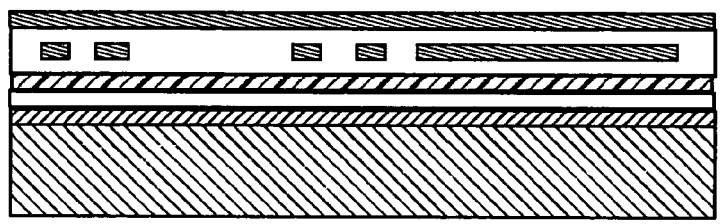
Figure 2C:
Figure 2C:
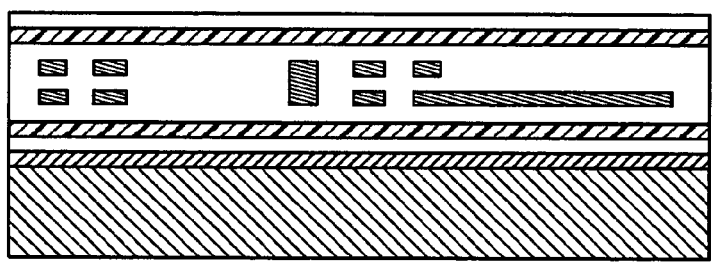
Figure 2D:
FIG. 2D depicts a device of the invention having an exemplary structure as associated with a substrate.
Figure 2D:
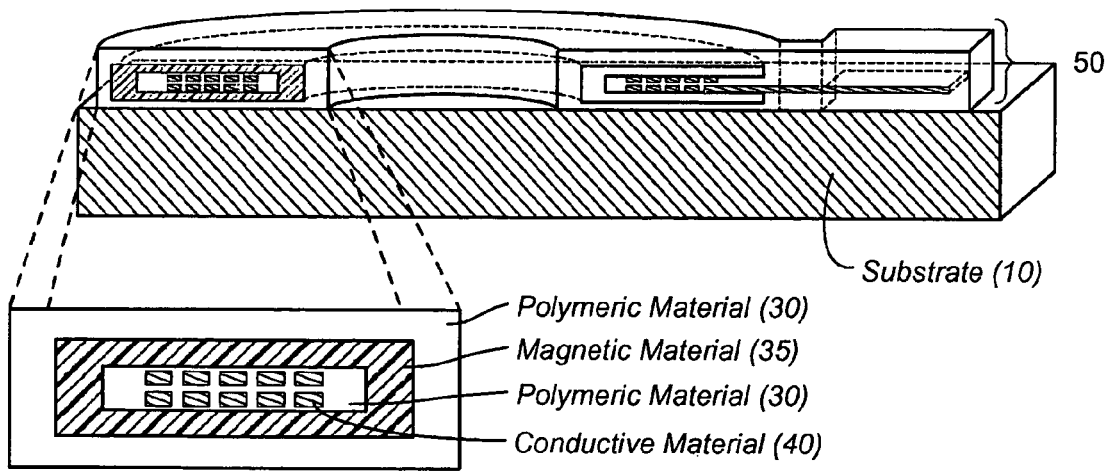
Figure 2E:
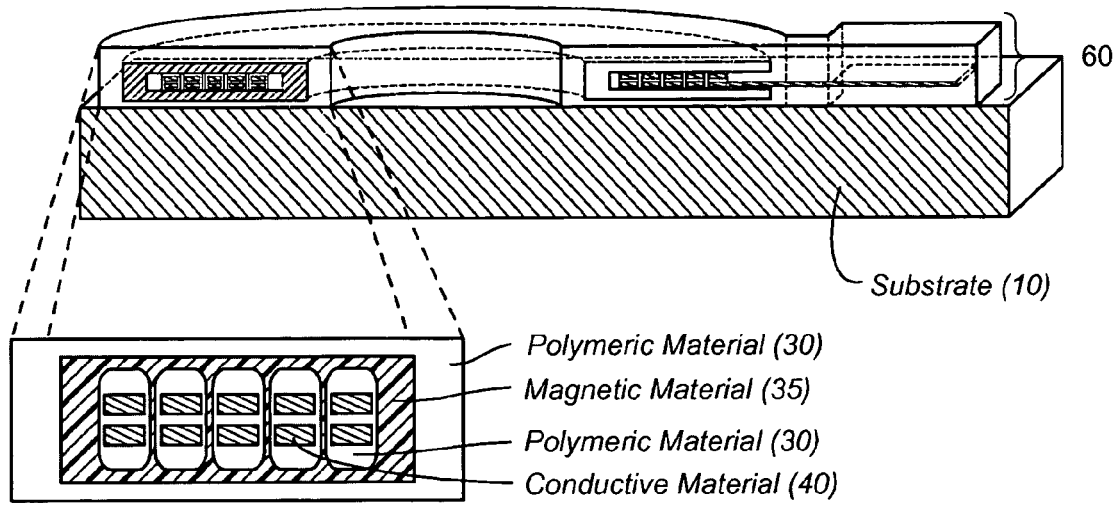
FIG. 2E depicts a device of the invention having an exemplary structure as associated with a substrate.
Figure 3:
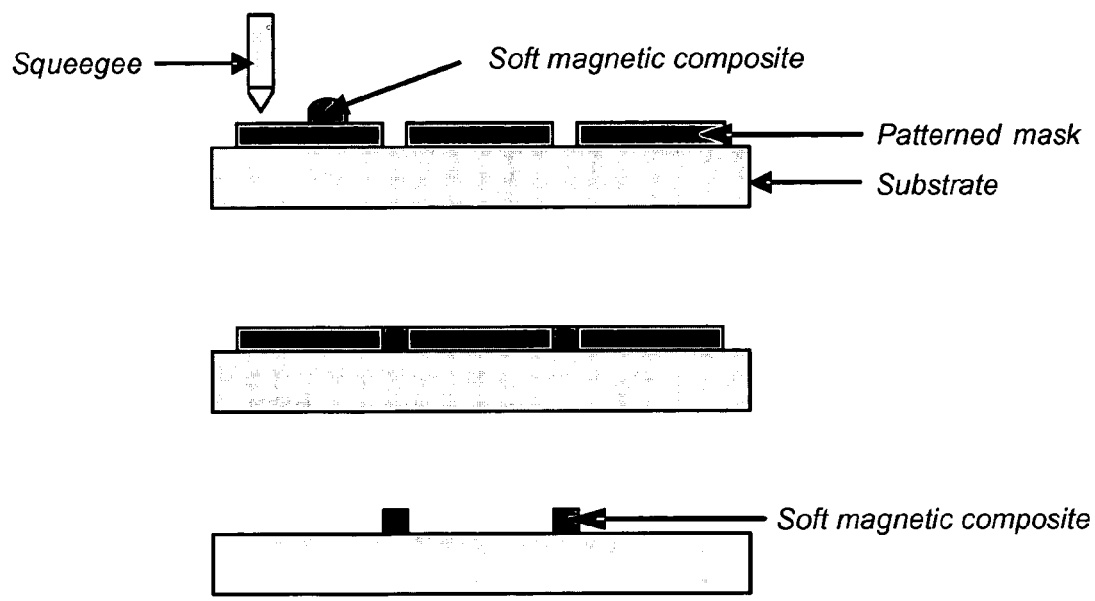
FIG. 3 depicts a method for depositing a magnetic material.

Exemplary deposition and patterning processes are provided in FIGS. 2A through 2C and in FIG. 3. It is understood that the manufacture of a device of the invention includes known method of integrated circuit (IC) fabrication, including metal-etch and lift-off methods. Referring to FIG. 2 generally, a cross-sectional view of an exemplary method for micro-fabrication of a device is provided. Referring to FIG. 2A, a sacrificial first layer of resist 20 is optionally deposited on a substrate 10. The deposition is optional because removal of the substrate subsequent to manufacture of the device can be accomplished by any suitable technique, including those that do not require the presence of a sacrificial layer between the substrate and the multilayer device. Accordingly, a first layer of polymeric material (e.g., parylene) 30 is deposited on the substrate 10 or the resist 20. A first layer of a magnetic material 35 is deposited on the layer of polymeric material. A second layer of polymeric material is deposited on the magnetic material. A first layer of conductive material (e.g., metal) 40 is deposited on the second layer of polymeric material 30. Referring to FIG. 2B, the initial layers of non-conductive polymeric material, conductive material and magnetic material have been deposited and patterned according to techniques known to the skilled artisan. For example, FIG. 3B depicts a method for depositing magnetic material using screen printing technology. Alternatives methods of depositing and patterning various layers of materials are discussed throughout the specification. Accordingly, referring to FIG. 2C, an additional layer of polymeric material 30 is deposited on a second layer of conductive layer that has been patterned. An additional layer of magnetic material is deposited followed by another layer of polymeric material. By this method multilayer devices are microfabricated to include a magnetic material in proximity to a conductive material and to enhance the ability of the conductive material to function as an RF coil.

The term "substrate" refers to any material upon which device processing may be performed, such as silicon. Materials can be deposited using conventional methods, such as, for example, chemical vapor deposition (CVD), plasma enhanced chemical vapor deposition (PECVD), spin coating, physical vapor deposition (PVD) among other deposition methods.

The polymeric material can include the following properties: a dielectric constant of about 2 to 4 at 60 Hz; an elongation break at about 10% to 300%; and a water absorption rate of about 0.01% to 0.10% per 24 hrs. In other embodiments, the polymeric material can include the following properties: a tensile strength of about 30 MPa to 80 MPa; and a gas permeability coefficient of about 0.50 to 2000 $cm^3$-mil/100 in 24 hr at 1 atm at 23° C.

"Patterning" is a process that defines regions for etching features. The feature may be, for example, a sub-micron feature. A feature can be extended into the polymeric material by etching, using, for example, a reactive ion etch process. A suitable etchant may be selected based upon the composition of the polymeric layer. Exemplary etchants include fluorocarbons, hydrofluorocarbons, sulfur compounds, oxygen, nitrogen, carbon dioxide, etc. Generally the feature 60 is aligned with a conductive sub-layer 40 such that contact may be made thereto. For embodiments in which an optional etch stop layer has been formed atop the conductive sub-layer, the etch stop layer may be removed by a suitable etchant in order to expose the conductive sub-layer.

In another embodiment, "lift-off" based fabrication can be used to manufacture a device of the invention. In semiconductor fabrication, the term 'lift-off' refers to the process of creating patterns on the wafer surface through an additive process, as opposed to patterning techniques that involve subtractive processes, such as etching. Briefly, a pattern is defined on a substrate using resist. A film is blanket-deposited all over the substrate, covering the resist and areas in which the resist has been cleared. During the actual lifting-off, the resist under the film is removed with solvent, taking the film with it, and leaving only the film which was deposited directly on the substrate. Depending on the type of lift-off process used, patterns can be defined with extremely high fidelity and for very fine geometries. The skilled artisan will recognize that any deposited film can be lifted-off. Instead of the chemical etch process described above, a lift-off resist layer can first be spun and patterned, and the conductive material subsequently deposited. When the resist is removed, the conductive material remaining is in the pattern defined by the absence of the resist.

Figure 6A:
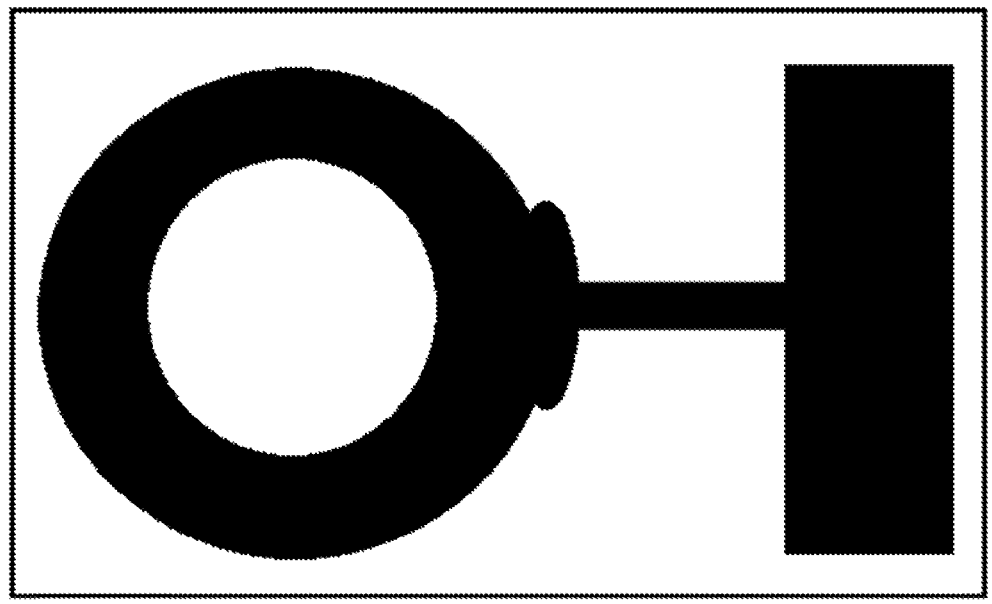
FIGS. 6A and 6B depict devices of the invention.
Figure 6B:
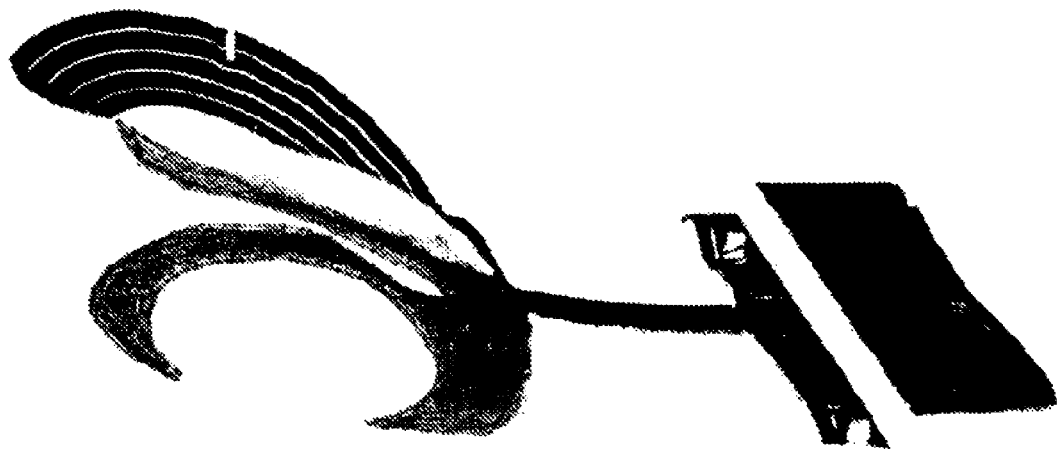

A device fabricated according to an "etch" or "lift-off" method can be heat formed using an existing mold because of the unique properties of the thin polymer material and the conductive structure. A fabricated device before and after heat-forming at 190° C. is shown in FIG. 6A and FIG. 6B, respectively. The process of heat forming the device is useful for molding the device to conform to a region of implantation in a biological environment. Thus, a microdevice of the invention can be contoured to fit a tissue associated with a particular biological environment.

Micro electro mechanical systems (MEMS) emerged with the aid of the development of integrated circuit (IC) fabrication processes, in which sensors, actuators, and control functions are co-fabricated in silicon. As described above, surface micro-machining builds structures on the surface of the silicon by depositing thin films of 'sacrificial layers' and 'structural layers' and by removing eventually the sacrificial layers to release the mechanical structures. The dimensions of these surface micro-machined devices can be several orders of magnitude smaller than bulk-micromachined devices. In addition, silicon-based micromechanical devices can be integrated into microelectronic processing systems such as CMOS (Complementary Metal-Oxide-Semiconductor), as known to one of skill in the art.

As used herein, the terms "micro electro mechanical systems/structures", "MEMS", "IMEMS", "micromachined structures" and any variations thereof, may generally be understood to comprise any miniature device combining, or otherwise capable of being suitably adapted to combine electrical and/or mechanical components that may be at least partially fabricated with batch-processing techniques. Moreover, the terms "MEMS", "IMEMS", "micromachined structures", "micro electro mechanical systems/structures" and any variations thereof may also be generally understood to comprise any miniature electromechanical device generally requiring at least temporary protection of spatially active elements during, for example, device packaging; whether such devices are now known or hereafter developed or otherwise described in the art. Such micro electro mechanical devices may be sealed or otherwise optionally configured for at least partial exposure to their operating environment; such as in the case of, for example, microsensor devices implanted in biological environments. Additionally, use of the term "microelectronic" may generally be understood to refer to any miniature electronic device and/or component that may or may not exhibit micro electro mechanical properties; for example, transistors of an IC element may be understood to comprise "microelectronic" devices that are generally not "micro electro mechanical" (i.e., IC transistors generally do not comprise spatially active elements) while RF MEMS switches may be understood to comprise "micro electro mechanical" devices that generally may also be classified as "microelectronic" in nature. Use of the term "plastic" is intended to include any type of flowable dielectric material. The term "film" may be used interchangeably with "coating" and/or "layer", unless otherwise indicated.

Previous methods for producing hand-wound coils are not suitable for fabricating MEMS devices for implantation in, for example, a biological environment, because the size and rigidity of the coil contributes to tissue degradation in the region of implantation. Thus, previous mechanisms for micro-fabrication of MEMS devices are unlikely to produce devices containing RF coils that are suitable for use in biological systems. Accordingly, the devices and systems provided herein are designed to avoid fixed electrical connections through, for example, the skin into the body. The devices and systems presented herein are designed for use with wireless power and data transmission implemented in practice through the use of an inductive link. A device of the invention can act as a transceiver for implanted systems such as hearing aids, implantable pacemakers, defibrillators, functional electrical stimulation devices such as cochlear implants, ocular implants and other organ assist or replacement devices.

FIG. 2D and FIG. 2E depict two exemplary geometries of the coil with a magnetic material core determined by simulations in terms of high magnetic flux and induced current considerations. The basic structure comprises two layers of magnetic material with conductive wires in between. In the second design (i.e., exemplary structure 2), magnetic material rings are deposited in the space between conductive material to distribute the magnetic field vertically. In order to form a closed circuit with two perimeter contacts, at two layers of conductive wires are fabricated using metals, conductive polymers, or other conductive materials, and interconnected by a via contact defined using oxygen plasma etching. Polymers (e.g. parylene C) can be used as insulating and packaging materials, and different coil profiles can be defined using oxygen plasma etching or excimer laser ablation, or other available techniques. Finally, the whole thin film can be released from substrate using a resist material as a sacrificial layer. For the further integration with other MEMS devices, ASICs and discrete electrical components, the connection pads can be replaced by flexible cables fabricated using polymer/metal/polymer thin film techniques.

Higher power densities and energy transfer efficiencies can be achieved for power applications using devices provided herein. In addition, encapsulating conductive material and magnetic material in a non-conductive polymeric material, such as parylene, allows for such a device to function under various environmental conditions. Accordingly, such devices are biocompatible and have a small size for implantation through small surgical incisions. The whole device can be completely microfabricated and integrated with other MEMS devices, discrete electrical components, and ASICs. High permeability materials, such as soft magnetic materials and Nickel, can be used as the magnetic material. Alternatively, soft magnetic composite materials in which powder magnetic material, ferrites and other magnetic powders, are mixed with polymers can be used instead of using bulk magnetic materials.

Spin-coating or screen printing technology may be employed to fabricate the magnetic core using soft magnetic composite materials. FIG. 3 shows the schematic for printing process. Instead of using electroplating technique, the soft magnetic composite can be deposited through a mask made by resist or other polymer materials. After the mask is removed, the magnetic composite remaining is in the pattern defined by the mask. In view of the methods provided herein, stack structures with multiple layers of magnetic material thin film can be microfabricated to achieve flexibility of the device. Accordingly, multi-stack structure of RF coil can be microfabricated by alternating, e.g., parylene layer, metal layer, and magnetic material layer deposition.

The examples set forth above are provided to give those of ordinary skill in the art a complete disclosure and description of how to make and use the embodiments of the devices, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of the invention have been described. Nevertheless, it will be understood that various modifications may be made without departing from the spirit and scope of the invention. Accordingly, other embodiments are within the scope of the following claims.

What is claimed is:
1. A device comprising the following components:
a) a conductive material configured to produce an electromotive force in the presence of a predetermined magnetic field density, wherein the predetermined magnetic field density is a modulated magnetic field specific to data transmission;
b) a magnetic material comprising a metal alloy selected from the group consisting of Perm-magnetic material, Fe—Ni magnetic material, Mo-perm-magnetic material, Mu-metal, M-1040, supermagnetic material and ultraperm configured to, in the presence of the predetermined magnetic field density, increase magnetic field density in proximity to the conductive material and induce an electromotive force in the conductive material that is higher with the magnetic material than without the magnetic material;
c) a polymeric material configured to provide chemical resistance and a barrier to moisture and oxygen,
wherein the magnetic material and the conductive material are encapsulated in the polymeric material, wherein the conductive material is surrounded by the magnetic material, wherein the conductive material and magnetic material are separated from one another by polymeric material such that the magnetic material increases the magnetic field density in proximity to the conductive material and wherein the components are assembled to provide a coil device comprising at least one structure that functions as a radio-frequency coil.
2. The device of claim 1, wherein the device supports wireless data and/or power transmission.

3. The device of claim 1, wherein the magnetic material is characterized as having high magnetic permeability, low coercivity, and low magnetostriction.

4. The device of claim 1, wherein the magnetic material is an alloy comprising nickel and iron.

5. The device of claim 4, wherein the alloy comprises about 80% nickel and about 20% iron.

6. The device of claim 4, wherein the alloy comprises about 45% nickel and about 55% iron.

7. The device of claim 6, wherein the device has a thickness from about 0.1 micron to about 10 microns.

8. The device of claim 1, wherein the polymeric material comprises the following properties:
   i) a dielectric constant of about 2 to 4 at 60 Hz;
   ii) an elongation break at about 10% to 300%;
   iii) a water absorption rate of about 0.01% to 0.10% per 24 hrs.

9. The device of claim 8, wherein the polymeric material further comprises the following properties:
   iv) a tensile strength of about 30 MPa to 80 MPa;
   v) a gas permeability coefficient of about 0.50 to 2000 $cm^3$-mil/100 in 24 hr at 1 atm at 23° C.; and
   vi) a moisture vapor transmission rate of less than 2.0 g-mil/100 in 24 hr at 90% relative humidity and 37° C.

10. The device of claim 9, wherein the gas permeability coefficient is from oxygen, nitrogen, carbon dioxide, hydrogen sulfide, sulphur dioxide or chlorine.

11. The device of claim 10, wherein the gas permeability coefficient for oxygen is less than 40 $cm^3$-mil/100 in 24 hr at 1 atm and at 23° C.

12. The device of claim 1, wherein the device has a thickness from about 0.05 micron to about 50 microns.

13. The device of claim 1, wherein the polymeric material comprises at least one of a parylene, an acrylic, a siloxane, xylene, an alkene, styrene, an organosilane, an organosilazane, an organosilicone, a PDMS (poly-di-methyl-siloxane) or a polyimide.

14. The device of claim 13, wherein the parylene is parylene N, parylene C, parylene D, parylene A, parylene AM, parylene F, parylene HT, or combinations thereof.

15. The device of claim 1, wherein the conductive material receives power and/or data from an external source by inductively coupled radio-frequency (RF) telemetry.

16. The device of claim 1, wherein the conductive material comprises at least one of a conductive polymer, platinum, platinum grey, platinum black, gold, iridium, titanium, chromium, copper, aluminum, iridium oxide, chromium oxide, silver oxide, indium zinc oxide, indium tin oxide, silicon oxide, silicon nitride, silicon oxynitride, aluminum oxide, aluminum nitride, aluminum oxynitride, zinc oxide, indium oxide, tin oxide, cadmium tin oxide, cadmium oxide, magnesium oxide, and combinations thereof.

17. The device of claim 1, comprising multiple layers of the polymeric material.

18. The device of claim 1, comprising multiple layers of the conductive material.

19. The device of claim 1, comprising multiple layers of the magnetic material.

20. The device of claim 1, wherein the radio frequency coil is an intraocular or extraocular coil.

21. The device of claim 20, wherein the device is contoured to conform to a region of implantation in a biological environment.

22. The device of claim 1, wherein the device is suitable for association with a biological system.

23. The device of claim 1, wherein the conductive material generates a magnetic field when contacted with an electromotive force.

24. A device comprising a plurality of layers of successively deposited material, wherein the deposition of each layer of material comprises:
   a) deposition of at least one first layer of polymeric material that provides chemical resistance and provides a barrier to moisture and oxygen;
   b) deposition of at least one layer of conductive material that supports wireless data and power transmission, wherein the conductive material is encapsulated in the polymeric material;
   c) deposition of at least one layer of magnetic material comprising a metal alloy selected from the group consisting of Perm-magnetic material, Fe—Ni magnetic material, Mo-perm-magnetic material, Mu-metal, M-1040, supermagnetic material and ultraperm on the at least one layer of polymeric material that, in the presence of a predetermined magnetic field density, wherein the predetermined magnetic field density is a modulated magnetic field specific to data transmission, increases magnetic field density in proximity to the conductive material and induces an electromotive force in the material that is higher with the magnetic material than without the magnetic material; and
   d) deposition of at least one second layer of polymeric material encapsulating the at least one layer of magnetic material;
   selectively patterning each layer,
   wherein a coil structure resulting from the deposition and patterning provides at least one structure that can function as a radio-frequency coil.

25. A system comprising:
   a first element comprising a device of claim 1 or claim 24;
   a second element inductively linked to the first element, the second element comprising:
      a mechanism for generating a magnetic field that contacts the first element; and
      a mechanism for generating radio frequency (RF) telemetry that contacts the first element;
   an electrode having a first end operably linked to the first element and a second end operably linked to an array.

26. The system of claim 25, wherein the first element is implanted in a biological system.

27. The system of claim 26, wherein the biological system is an eye.

28. The system of claim 25, wherein the device is an intraocular or extraocular coil.

29. The system of claim 25, wherein the first element comprises an integrated circuit.

30. The system of claim 25, wherein the second element is external to the biological system.

31. The system of claim 25, wherein the second element is a transmitter comprising a coil.

32. The system of claim 25, wherein the first element further includes an amplifier.

33. The system of claim 25, wherein the array is a retinal array.

34. The system of claim 33, wherein the retinal array is associated with nerve cells.

35. The system of claim 34, wherein the nerve cells comprise retinal tissue.

* * * * *